US00PP34073P2

(12) United States Plant Patent
Adcock et al.

(10) Patent No.: US PP34,073 P2
(45) Date of Patent: Mar. 29, 2022

(54) ***THUJA* TREE NAMED 'CMA04271964'**

(50) Latin Name: ***Thuja plicata* x *standishii***
Varietal Denomination: CMA04271964

(71) Applicant: Adcock's Nursery, Fuquay-Varina, NC (US)

(72) Inventors: Jeffrey C. Adcock, Fuquay-Varina, NC (US); Richard S. Gurkin, Fuquay-Varina, NC (US)

(73) Assignee: Adcock's Nursery, Fuquay-Varina, NC (US)

( * ) Notice: Subject to any disclaimer, the term of this patent is extended or adjusted under 35 U.S.C. 154(b) by 0 days.

(21) Appl. No.: 17/300,837

(22) Filed: Nov. 23, 2021

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00
See application file for complete search history.

*Primary Examiner* — Keith O. Robinson
(74) *Attorney, Agent, or Firm* — Samuel R. McCoy, Jr.

(57) ABSTRACT

A new and distinct *Thuja* tree named 'CMA04271964' which is characterized by a relatively small stature, vigorous rooting, slow vegetative growth, a freely branching and densely foliaged growth habit, shortened internodal spacing, and greyed-orange suffusion of the juvenile lateral foliage and juvenile branchlets. The claimed plant propagates successfully by semi-hardwood stem cuttings and has proven to be uniform and stable in the resulting generations.

3 Drawing Sheets

Latin name of the genus and species: The Latin name of the genus and species of the novel variety disclosed herein is *Thuja plicata* x *standishii.*

Variety denomination: The inventive variety of *Thuja plicata* x *standishii* disclosed herein has been given the variety denomination 'CMA04271964'.

BACKGROUND OF THE INVENTION

The present invention relates to a new and distinct perennial variety of *Thuja plicata* x *standishii*, which has been given the variety denomination of 'CMA04271964'. Both *Thuja plicata* and *Thuja standishii*, commonly known as arborvitae, are coniferous evergreens of the cypress family Cupressaceae. While members of the same family, their origins and morphological characteristics vary greatly. *Thuja plicata* is a large evergreen tree that is native to northwestern North America, whereas *T. standishii* is a small to medium evergreen that is native to southern and central Japan. *T. plicata* can grow to a size of 70 ft. tall by 25 ft. wide, whereas *T. standishii* is typically reported to grow to more than 30 ft. tall and 15 ft. wide, at maturity. Despite the difference in size, both species have similar pyramidal growth habits and foliage with sprays of scale-like foliage borne on horizontal to ascending branches and branchlets. Both are hardy in USDA Zones 5 through 7. The most prolific hybrid of the two species, and the parent plant of the candidate variety, *Thuja plicata* x *standishii* 'Green Giant' is favored by home gardeners and professionals alike for its vigorous growth habit, intermediate size, pyramidal to conical shape and rich green foliage color that persists outstanding throughout its hardiness range.

Parentage: The claimed tree originated as a naturally-occurring, whole-plant mutation of *Thuja plicata* x *standishii* 'Green Giant' (not patented) which was discovered at a commercial tree nursery in Fuquay-Varina, N.C. In April of 2014, the claimed plant was discovered growing amongst a cultivated population of 'Green Giant'. Said mutation exhibited a dwarfed growth habit when compared to other 'Green Giant' trees in the population and other specimens that typify the species. The tree was isolated and grown for an additional three years to confirm the distinctness and stability of the characteristics initially observed. Upon further evaluation and confirmation of the desirable traits, the claimed tree was ultimately selected for commercial production in February of 2017.

Asexual Reproduction: In 2016, 'CMA04271964' was first asexually reproduced by way of semi-hardwood stem cuttings in Fuquay-Varina, N.C. The claimed tree was found to asexually reproduce in uniform and stable manner and three successive cycles of vegetative propagation have proven to be true to type.

SUMMARY OF THE INVENTION

The following characteristics have been repeatedly observed and represent the distinguishing characteristics of the new *Thuja* tree, 'CMA04271964'. These traits, in combination, distinguish 'CMA04271964' as a new and distinct cultivar.

1. 'CMA04271964' exhibits a relatively small stature, with a freely branching and densely foliaged growth habit; and
2. 'CMA04271964' exhibits relatively fast, vigorous rooting; and
3. 'CMA04271964' exhibits slower vegetative growth; and
4. 'CMA04271964' exhibits a main stem and lateral branches with shortened nodal spacing; and
5. 'CMA04271964' exhibits distalmost lateral foliage and, occasionally, branchlets which are lightly suffused with a mixture of light yellow-green and greyed-orange, when exposed to natural light.

BOTANICAL DESCRIPTION OF THE PLANT

Figure 1:
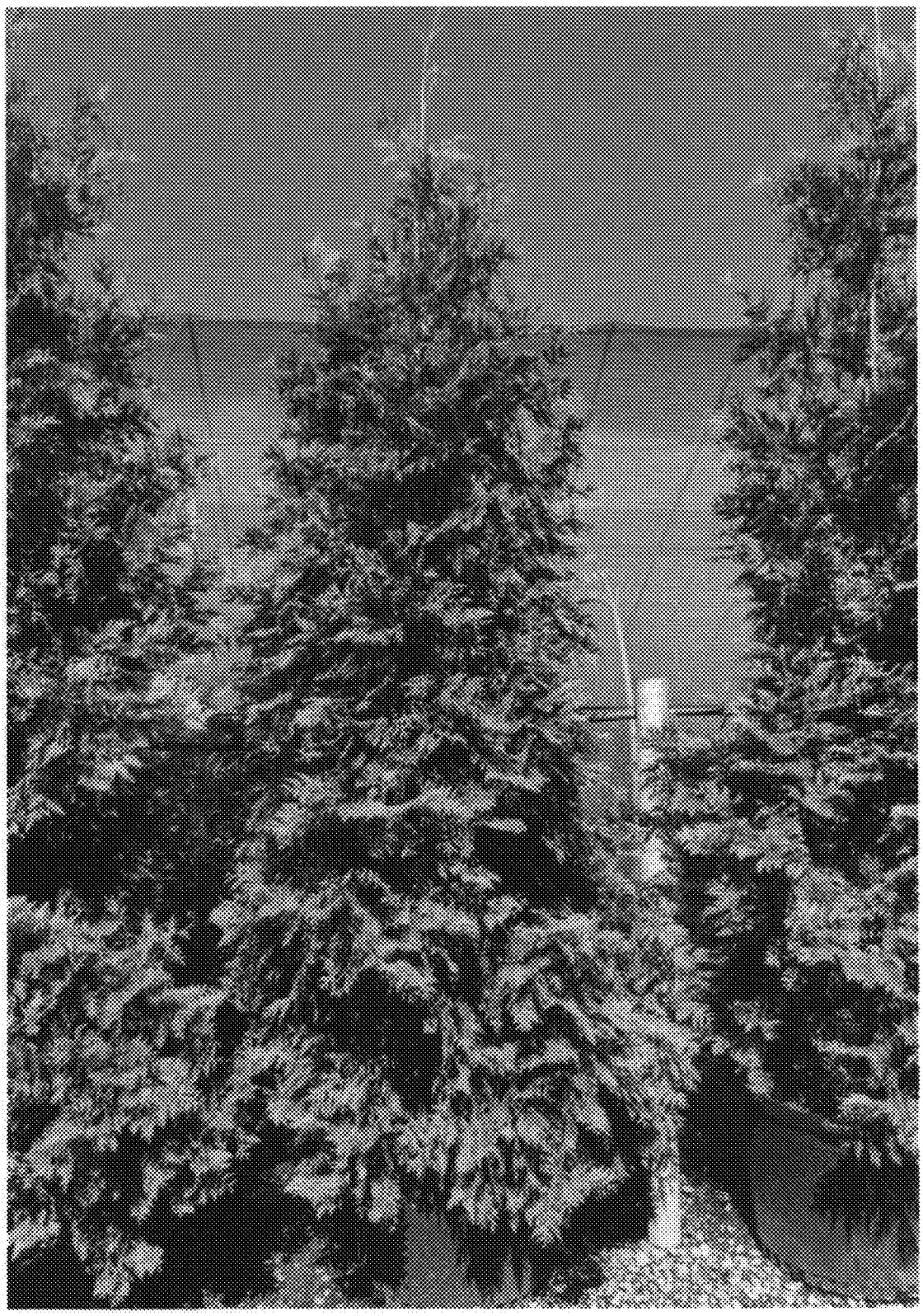
FIG. 1 illustrates, as nearly true as it is reasonably possible to make the same in color photographs of this type, a container-grown 'CMA04271964' tree at approximately 2.5 years of age, during early autumn in Fuquay-Varina, N.C.
Figure 2:
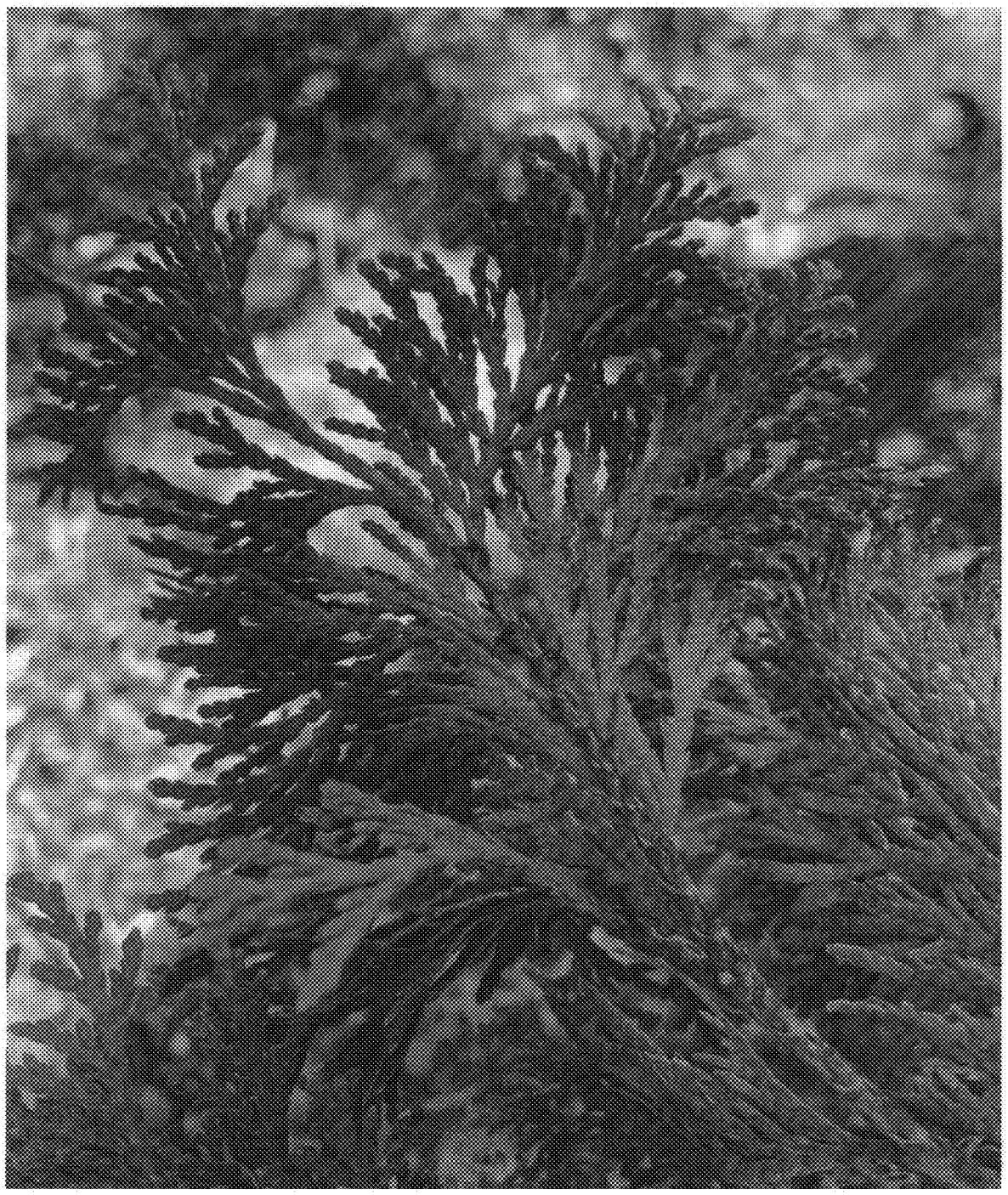
FIG. 2 illustrates, as nearly true as it is reasonably possible to make the same in color photographs of this type, the adaxial surface of the branchlets of 'CMA04271964'.
Figure 3:
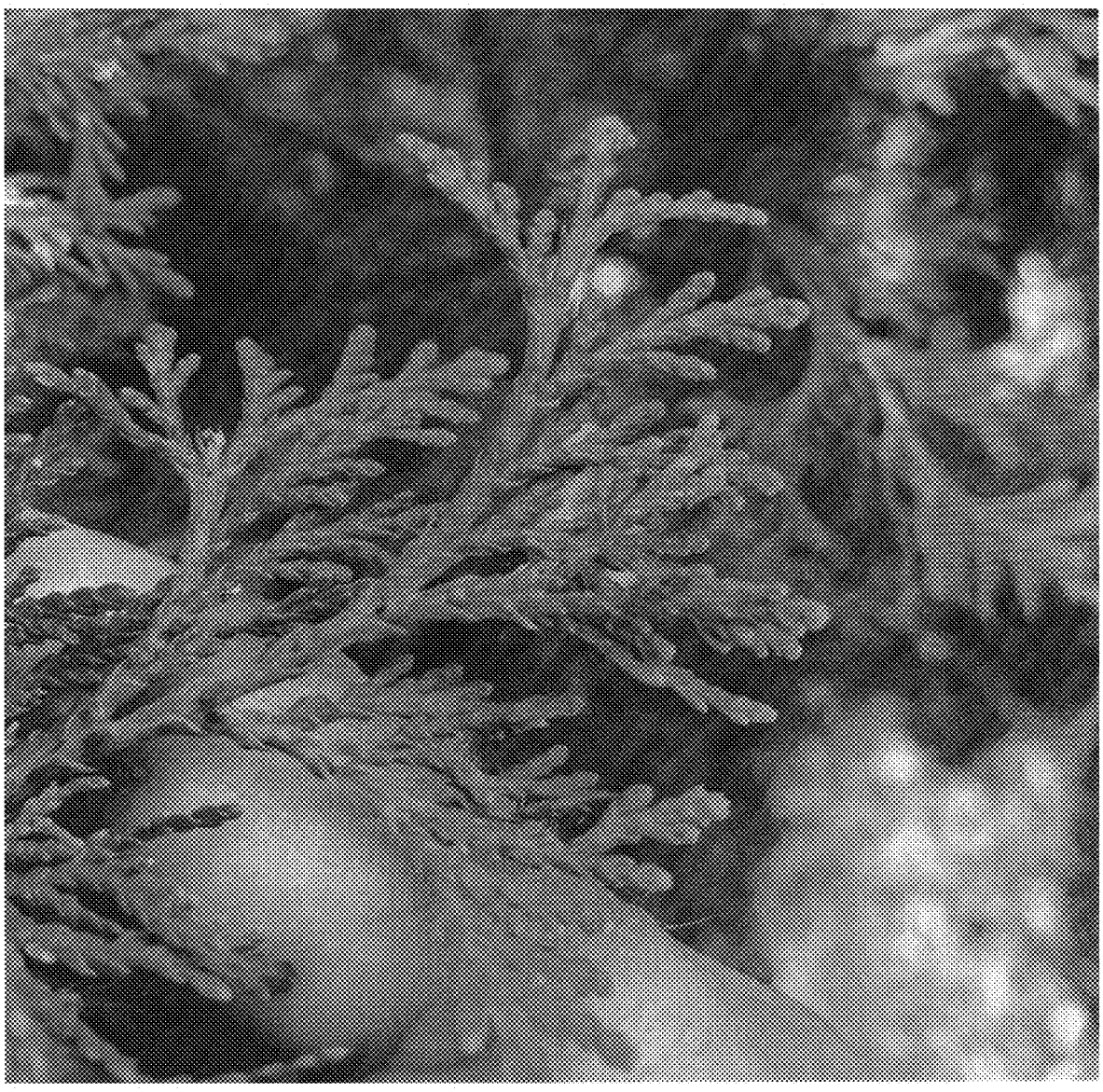
FIG. 3 illustrates, as nearly true as it is reasonably possible to make the same in color photographs of this type, the abaxial surface of the branchlets of 'CMA04271964'.

The following is a detailed botanical description of a new and distinct *Thuja plicata* x *standishii* plant cultivar known as 'CMA04271964'. Unless otherwise stated, observations were made on a container-grown 5.5 year-old tree produced in a 15-gallon nursery container at a commercial plant nursery in Fuquay-Varina, N.C. Semi-hardwood cuttings were rooted into 36-cell propagation trays in February of 2016 and subsequently potted into 1-gallon nursery containers in December of 2017. These 1-gallon containers were later potted into 3-gallon nursery containers in June of 2018. These 3-gallon trees were grown in an unheated greenhouse through the winter of 2018 and 2019 before being potted into the 15-gallon containers in April of 2019. Once shifted into these 15-gallon containers, the trees were moved outside and grown in full sun with overhead irrigation, with no winter protection. In May of 2020, these trees were moved to an area that provided cable support of the trees, as is typical with convention production of *Thuja* sp., and provided irrigation by way of spray stakes in the pots. Young trees were provided a moderate rate of an 8 to 9 month slow-release granular fertilizer at the time of potting into the 1-gallon containers and further supplemented with a 5 to 6 month slow-release granular fertilizer throughout the course of production, as needed. Pest countermeasures were employed as needed. Observation data was recorded in July of 2021.

Those skilled in the art will appreciate that certain characteristics will vary with older or, conversely, younger plants. 'CMA04271964' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 1986 edition except where common terms of color are used.

A botanical description of 'CMA04271964' and comparisons with the parent and most similar commercial cultivar are provided below.

General plant description:

*Plant habit*.—Evergreen conifer with a conical shape and upright attitude.

*Tree crown profile*.—Pyramidal.

*Dimensions*.—Approximately 4.25 meters tall and 2.0 meters wide at 8 years of age.

*Environmental tolerances*.—Hardy in US Hardiness Zones 5 through 9; prefers cooler climates with moist, loamy soils and full to filtered sun exposure but will tolerate hotter, dryer conditions.

*Pest and disease susceptibility or resistance*.—Plants have not been observed to be susceptible or resistant to pathogens and pests common to *Thuja* sp.

*Propagation*.—Propagation is accomplished using semi-hardwood stem cuttings.

*Time to produce a rooted* 36-*cell rooted cutting*.—Unrooted cuttings are typically planted in mid-January in an unheated greenhouse with bottom heat in Fuquay-Varina, N.C. These cuttings are typically ready for transplant into larger containers by mid to late August.

*Crop time*.—Approximately 18 months are needed to produce a well rooted and marketable 15-gallon nursery container, from a 3-gallon container.

Root system:

*Description*.—A network of fibrous, non-fleshy roots.

*Rooting habit*.—Freely branching, moderately dense, and relatively shallow in the soil profile.

Stems:

*Branching habit*.—A dominant, near-vertical central main stem, typically unbranched, gives rise to an abundance of lateral branches, themselves freely branching into primary, secondary, and tertiary branchlets.

*Main stem; central leader*.—Attitude — Erect; near vertical. Aspect — Generally rounded. Diameter — 5.0 cm, at the base of the trunk. Internodal spacing — 20 mm. Strength — Strong. Texture — Smooth and glabrous; becoming progressively fissured and furrowed with age, at and towards the base or trunk of the tree. Distally, the main stem is densely covered with persistent, desiccated lateral leaves. Luster — Matte to slightly glossy. Color, distalmost juvenile wood — Both the persistent lateral leaves and the surrounding wood are colored greyed-orange, nearest to a mixture of RHS 165B, 165C and 172A. Color, mature basal wood — Brown, nearest to 200D yet lighter, and suffused with a combination of greyed-green and greyed-orange, RHS 197A and 165A; fissures are colored greyed-green, RHS 197B.

*Lateral branches*.—Attitude — Near the base of the tree, lateral branches are at an angle of approximately 90 degrees to the main stem, and ascending along their length; distally, the lateral branches are more upright at an angle of approximately 45 to 60 degrees to the main stem. Aspect — Round. Diameter — 1.1 cm at the base. Length — Basal branches reach approximately 42 cm in length from the trunk to the distalmost node. Internodal spacing — Ranging from 10 to 20 cm, with an average length of 15 mm. Texture — Smooth and glabrous. Distally, the lateral branches are densely covered with persistent, desiccated lateral leaves. Luster — Matte to slightly glossy. Color, juvenile — Both the persistent lateral leaves and the surrounding wood are colored greyed-orange, nearest to a mixture of RHS 165B, 165C and 172A. Color, mature — Brown, nearest to 200D yet lighter, and suffused with a combination of greyed-green and greyed-orange, RHS 197A and 165A. Moderately glaucous at all stages.

*Branchlets*.—Attitude — Outward; occasionally pendulous. Aspect — Flattened in a linear plane with the lateral branches; occasionally exhibiting an axial twist or spiraled aspect. Dimensions — The dimensions of the entire branchlet (comprised of primary, secondary and tertiary branchlets) is highly variable, depending on the age of the individual branchlet. Individual branchlets are approximately 6.5 mm wide and 4.0 mm high and variable in length. Texture and luster, juvenile — Glabrous and glossy. Texture and luster, mature — Glabrous and slightly glossy. Color, juvenile branchlets — Branchlets are entirely concealed by the facial, adpressed foliage. Therefore, branchlet color is the same as that of the facial leaves. Color, older branchlets — Branchlets are largely concealed by the lateral, adpressed foliage. Therefore, the general coloration of older branchlets is the same as that of the lateral leaves; where exposed, lateral branch color is greyed-orange, nearest to a mixture of RHS 165B, 165C and 172A.

Foliage: Leaves are dimorphic with smaller adpressed, scale-like leaves borne on leading juvenile branchlets and larger rhombic leaves borne along lateral branches and older branchlets.

*Facial leaves of juvenile branchlets*.—Arrangement — Alternating decussate pairs of adpressed facial leaves, which are tightly held along the entire length of the juvenile branchlets. Attachment — Sessile. Division — Simple. Shape — Scale-like. Aspect — Adpressed to branchlets; convex. Length — 5.0 mm. Width — 2.5 mm. Apex — Acute. Base — Bluntly decurrent. Margin — Entire; no undulation. Texture and pubescence, adaxial surface — Glabrous and glossy. Texture and pubescence, abaxial surface — Glabrous and slightly glossy. Color — Juvenile foliage, adaxial surface — Yellow-green, nearest to in between RHS 144A and 144B. Juvenile foliage, abaxial surface — Yellow-green, nearest to in between RHS 144A and 144B. Mature foliage, adaxial surface — Nearest to in between yellow-green and green, RHS 144A and 143B. Mature foliage, abaxial surface — Nearest to in between yellow-green and green, RHS 144A and 143B. Venation — Indistinguishable from the lamina under 20-times magnification. Petiole — Absent. Stipules — Absent.

*Lateral leaves of older branchlets and lateral branches*.—Arrangement — Alternating decussate pairs of lateral leaves, adpressed, and somewhat loosely held on distal portions of lateral branches and older branchlets. Attachment — Sessile. Division — Simple. Shape — Rhomboid. Aspect — Adpressed; apex is free. Length — 12.0 mm. Width — 4.0 mm. Apex — Acute. Base — Decurrent. Margin — Entire; no undulation. Texture and pubescence, adaxial surface — Glabrous and glossy. Texture and pubescence, abaxial surface — Glabrous and slightly glossy. Color — Juvenile foliage, adaxial surface — Yellow-green, nearest to in between RHS 144A and 144B. Juvenile foliage, abaxial surface — Yellow-green, nearest to in between RHS 144A and 144B. Mature foliage, adaxial surface — Yellow-green, nearest to in between RHS 144B and 144C, and suffused with a mixture of yellow-green and greyed-orange, RHS 151A, 163B, and 163C; becoming darker green toward the apex, nearest to in between yellow-green and green, RHS 144A and 143B. Mature foliage, abaxial surface — Yellow-green, nearest to in between RHS 144B and 144C, and suffused with a mixture of yellow-green and greyed-orange, RHS 151A, 163B, and 163C; becoming darker green toward the apex, nearest to in between yellow-green and green, RHS 144A and 143B. Venation — Indistinguishable from the lamina under 20-times magnification. Petiole — Absent. Stipules — Absent.

Inflorescence: To date, no flowering has been observed on the mother plant or any progeny therefrom.

Flower bud: To date, no flowering has been observed on the mother plant or any progeny therefrom.

Flower: To date, no flowering has been observed on the mother plant or any progeny therefrom.

Reproductive organs: To date, no flowering has been observed on the mother plant or any progeny therefrom.

Fruit and seed: To date, no fruiting has been observed on the mother plant or any progeny therefrom.

COMPARISON WITH THE PARENT PLANT

Plants of the new cultivar 'CMA04271964' differ from the parent, *Thuja* 'Green Giant' (not patented), by the characteristics described in Table 1.

TABLE 1

| Characteristic | 'CMA04271964' | 'Green Giant' |
|---|---|---|
| Tree height. | Significantly shorter than the 'Green Giant'; approximately 40 to 60 percent shorter. | Much taller than 'CMA04271964'. |
| Internode spacing. | Significantly shorter. | Significantly longer. |

COMPARISON WITH THE MOST SIMILAR *THUJA* CULTIVAR KNOWN TO THE INVENTOR

Plants of the new cultivar 'CMA04271964' are most similar to the commercial cultivar, *Thuja* 'BFC68' (U.S. Plant Pat. No. 26,684). A comparison of 'CMA04271964' with *Thuja* 'BFC68' is described in Table 2.

TABLE 2

| Characteristic | 'CMA04271964' | 'BFC68' |
|---|---|---|
| Plant vigor; rooting. | Faster rooting than 'BFC68'. | Slower rooting than 'CMA04271964'. |
| Expression of the yellow-green and greyed-orange suffusion of the distalmost lateral foliage and branchlets. | Consistently present; conspicuous. | Only occasionally present; when present, it is less conspicuous, relative to 'CMA04271964'. |

That which is claimed is:

1. A new and distinct variety of *Thuja* tree named 'CMA04271964', substantially as described and illustrated herein.

* * * * *